US011654252B2

(12) United States Patent
Hezkiahu

(10) Patent No.: US 11,654,252 B2
(45) Date of Patent: May 23, 2023

(54) HOUSING WITH SYRINGE HOLDING FEATURE

(71) Applicant: West Pharmaceutical Services, Inc., Exton, PA (US)

(72) Inventor: Ran Hezkiahu, Herzliya (IL)

(73) Assignee: West Pharmaceutical Services, Inc., Exton, PA (US)

( * ) Notice: Subject to any disclaimer, the term of this patent is extended or adjusted under 35 U.S.C. 154(b) by 250 days.

(21) Appl. No.: 16/651,943

(22) PCT Filed: Oct. 1, 2018

(86) PCT No.: PCT/US2018/053819
§ 371 (c)(1),
(2) Date: Mar. 27, 2020

(87) PCT Pub. No.: WO2019/068109
PCT Pub. Date: Apr. 4, 2019

(65) Prior Publication Data
US 2020/0282152 A1 Sep. 10, 2020

Related U.S. Application Data

(60) Provisional application No. 62/565,669, filed on Sep. 29, 2017.

(51) Int. Cl.
*A61M 5/24* (2006.01)
*A61M 5/34* (2006.01)
(Continued)

(52) U.S. Cl.
CPC .......... *A61M 5/346* (2013.01); *A61M 5/3129* (2013.01); *A61M 5/31566* (2013.01);
(Continued)

(58) Field of Classification Search
CPC .......... A61M 5/326; A61M 2005/3264; A61M 2005/3261; A61M 5/31578; A61M 2005/3268; A61M 2005/244
See application file for complete search history.

(56) References Cited

U.S. PATENT DOCUMENTS

| 6,171,283 B1 | 1/2001 | Perez et al. |
| 2004/0034323 A1 | 2/2004 | Manthey |

(Continued)

FOREIGN PATENT DOCUMENTS

| CN | 1229679 A | 9/1999 |
| CN | 1518463 A | 8/2004 |

(Continued)

OTHER PUBLICATIONS

Int'l Preliminary Report on Patentability dated Sep. 18, 2019 in Int'l Application No. PCT/US2018/053819.

(Continued)

*Primary Examiner* — Emily L Schmidt
(74) *Attorney, Agent, or Firm* — Blank Rome LLP

(57) ABSTRACT

A securing device for an injection device which receives a syringe with a proximal end portion having a radially outwardly projecting flange, has a body with proximal and distal end portions, an opening for accepting the syringe, an outer surface, and a proximal end surface for contacting a distally-facing surface of the flange when the syringe is advanced distally, preventing further advancement. A securing arm includes a free end; a base end fixed to the outer surface; a first portion extending radially outwardly from the base end to permit the flange to pass; and a second portion extending radially inwardly in a rest position, contacting the flange as the syringe is advanced. The securing arm is elastically flexible to allow the free end to move radially outwardly, allowing the advancing flange to pass, and is (Continued)

biased to the rest position to secure the flange and the syringe against proximal movement.

26 Claims, 11 Drawing Sheets

(51) Int. Cl.
  *A61M 5/31* (2006.01)
  *A61M 5/315* (2006.01)
  *A61M 5/32* (2006.01)

(52) U.S. Cl.
  CPC ...... *A61M 5/31578* (2013.01); *A61M 5/3202* (2013.01); *A61M 5/345* (2013.01)

(56) References Cited

U.S. PATENT DOCUMENTS

| | | |
|---|---|---|
| 2005/0187522 A1 | 8/2005 | Miller |
| 2006/0161114 A1 | 7/2006 | Perot et al. |
| 2008/0167611 A1 | 7/2008 | Miller |
| 2009/0318866 A1 | 12/2009 | Ferrari |
| 2011/0092915 A1 | 4/2011 | Olson et al. |
| 2013/0184655 A1* | 7/2013 | Lanzi .................. A61M 5/3135 604/241 |
| 2014/0039406 A1* | 2/2014 | Verespej ................. A61M 5/28 604/194 |
| 2015/0075520 A1 | 3/2015 | Kakuta et al. |

FOREIGN PATENT DOCUMENTS

| | | |
|---|---|---|
| CN | 201662686 U | 12/2010 |
| CN | 102058918 A | 5/2011 |
| CN | 102421472 A | 4/2012 |
| CN | 104411351 A | 3/2015 |
| CN | 104470563 A | 3/2015 |
| EP | 0864335 A2 | 9/1998 |
| RU | 2557896 C2 | 7/2015 |
| WO | 2013/146000 A1 | 10/2013 |
| WO | 2013159059 A1 | 10/2013 |

OTHER PUBLICATIONS

Int'l Search Report and Written Opinion dated Jan. 7, 2019 in Int'l Application No. PCT/US2018/053819.

* cited by examiner

HOUSING WITH SYRINGE HOLDING FEATURE

FIELD OF THE INVENTION

The present disclosure relates to the field of syringe housings, and in particular to a mechanism for securing a syringe within the body of a housing.

BACKGROUND

Prior devices in which a syringe is secured within a housing rely on adapters, and/or on friction between the adapter or the housing and the body of the syringe, typically are configured to secure a single size syringe.

SUMMARY OF THE DISCLOSURE

Briefly stated, an example of a securing device is described for an injection device which receives a syringe. The syringe has a barrel with a proximal end portion and a distal end portion, the proximal end portion having a radially outwardly projecting flange, with the flange having a proximally-facing surface and a distally-facing surface. The securing device includes a hollow body having a proximal end portion and a distal end portion. The body has an opening in the proximal end portion accessing an interior of the body for accepting the syringe. The body has a radially outwardly-facing outer surface and a proximal end surface. The proximal end surface of the body is configured to contact the distally-facing surface of the flange of the syringe when the syringe is advanced distally into the opening, so that the flange does not move distally past the proximal end surface of the body. A securing arm has a free end, a base end, a first portion, and a second portion. The base end is fixed to the outer surface of the body. The first portion extends radially outwardly from the base end beyond the proximal end surface of the body to form a radial flange clearance permitting the flange to pass the second portion as the syringe is advanced distally into the opening. The first portion further extends proximally from the base end beyond the proximal end surface to form a flange gap between the proximal end surface of the body and a distally-facing surface of the second portion. The second portion is located proximally with respect to the flange gap and extends at least partially radially inwardly toward the free end in a rest position of the securing arm. The second portion contacts the flange as the syringe is advanced distally into the opening. The securing arm is elastically flexible to permit at least the second portion to pivot radially outwardly relative to the body to allow the flange to pass the second portion as the syringe is advanced distally into the opening. The securing arm is biased to the rest position such that after the flange passes the second portion, the distally-facing surface of the second portion is configured to contact the proximally-facing surface of the flange to prevent the flange from moving proximally past the securing arm.

In some embodiments, the first portion of the securing arm extends substantially parallel to a longitudinal axis of the body and the second portion of the securing arm extends substantially parallel to the proximal end surface of the body.

In some embodiments, an inner surface of the second portion of the securing arm is curved with a radius of curvature that extends substantially radially into the body.

In some embodiments, the securing arm has a first flexibility with respect to radially outward movement of the free end of the securing arm with respect to the body, and a second flexibility with respect to proximal movement of the free end of the securing arm with respect to the body, and the first flexibility is greater than the first flexibility.

In some embodiments, the first portion of the securing arm has a first-portion length parallel to the longitudinal axis of the body, and the second portion of the securing arm has a second-portion length parallel to the proximal end surface of the body, and the second-portion length is about 2 to 3 times the first-portion length.

In some embodiments, the first portion of the second securing arm has a first-portion length parallel to the longitudinal axis of the body, and the second portion of the second securing arm has a second-portion length parallel to the proximal end surface of the body, and the second-portion length is at least about 2 to 3 times the first-portion length.

In some embodiments, the securing arm has a free end, a base end, a first portion, and a second portion. The base end is fixed to the outer surface of the body. The first portion extends radially outwardly from the base end beyond the proximal end surface of the body to form a radial flange clearance permitting the flange to pass the second portion as the syringe is advanced distally into the opening. The first portion further extends proximally from the base end beyond the proximal end surface to form a flange gap between the proximal end surface of the body and a distally-facing surface of the second portion. The second portion is located proximally with respect to the flange gap and extends at least partially radially inwardly toward the free end in a rest position of the securing arm. The second portion contacts the flange as the syringe is advanced distally into the opening. The securing arm is elastically flexible to permit at least the second portion to pivot radially outwardly relative to the body to allow the flange to pass the second portion as the syringe is advanced distally into the opening. The securing arm is biased to the rest position such that after the flange passes the second portion, the distally-facing surface of the second portion is configured to contact the proximally-facing surface of the flange to prevent the flange from moving proximally past the securing arm.

In some embodiments, the securing arm has a contoured surface for contacting the flange as the syringe advances distally. The contoured surface is configured so that at least the free end of the securing arm moves radially outwardly to allow the flange of the advancing syringe to pass.

In some embodiments, the contoured surface includes a beveled surface.

In some embodiments, the distally-facing surface of the second portion of the securing arm is configured so that a first portion of the distally-facing surface nearer the free end of the securing arm is positioned distally with respect to a second portion of the distally-facing surface nearer the base.

A hand-held injection device which can receive a syringe prefilled with a drug and having a needle includes a body having a proximal end portion and a distal end portion. The body has an opening in the proximal end portion accessing an interior of the body for accepting the syringe. The body has a radially-outwardly facing outer surface and a proximal end surface. The proximal end surface of the body is configured to contact the distally-facing surface of the flange of the syringe when the syringe is advanced distally into the opening, so that the flange does not move distally past the proximal end surface of the body. A securing arm has a free end, a base end, a first portion, and a second portion. The base end is fixed to the outer surface of the body. The first portion extends radially outwardly from the base end beyond the proximal end surface of the body to form a radial flange clearance permitting the flange to pass the first portion as the syringe is advanced distally into the opening. The first portion further extends proximally from the base end beyond the proximal end surface to form a flange gap between the proximal end surface of the body and a distally-facing surface of the second portion. The second portion is located proximally with respect to the flange gap and extends at least partially radially inwardly toward the free end in a rest position of the securing arm. The second portion contacts the flange as the syringe is advanced distally into the opening. The securing arm is elastically flexible to permit at least the free end to move radially outwardly relative to the body to allow the flange to pass the first portion as the syringe is advanced distally into the opening. The securing arm is biased to the rest position. After the flange passes the second portion, the distally-facing surface of the second portion is configured to contact the proximally-facing surface of the flange to prevent the flange from moving proximally past the securing arm. A needle guard is movable relative to the body proximally from a first position. The needle guard extends from the body distally, so as to be configured to cover, when the syringe is secured in the body, the needle as the needle extends from the lower housing distally, to a second position, wherein the needle guard is retracted relative to the tip of the needle so as to expose the tip of the needle. An upper housing is supported relative to the lower housing. The upper housing is configured to receive a manual force and move with respect to the lower housing distally from a pre-use position to a dispensed position in response to the manual force. A plunger rod is carried by the upper housing and movable with the upper housing so as to advance relative to the syringe when the upper housing is moved distally. Advancement of the plunger rod relative to the syringe causes the syringe to deliver the medication through the needle.

In some embodiments, a prefilled syringe is provided for insertion into the body to be secured by the securing device

BRIEF DESCRIPTION OF THE DRAWINGS

The foregoing summary, as well as the following detailed description of an example of a device according to the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION

Figure 1:
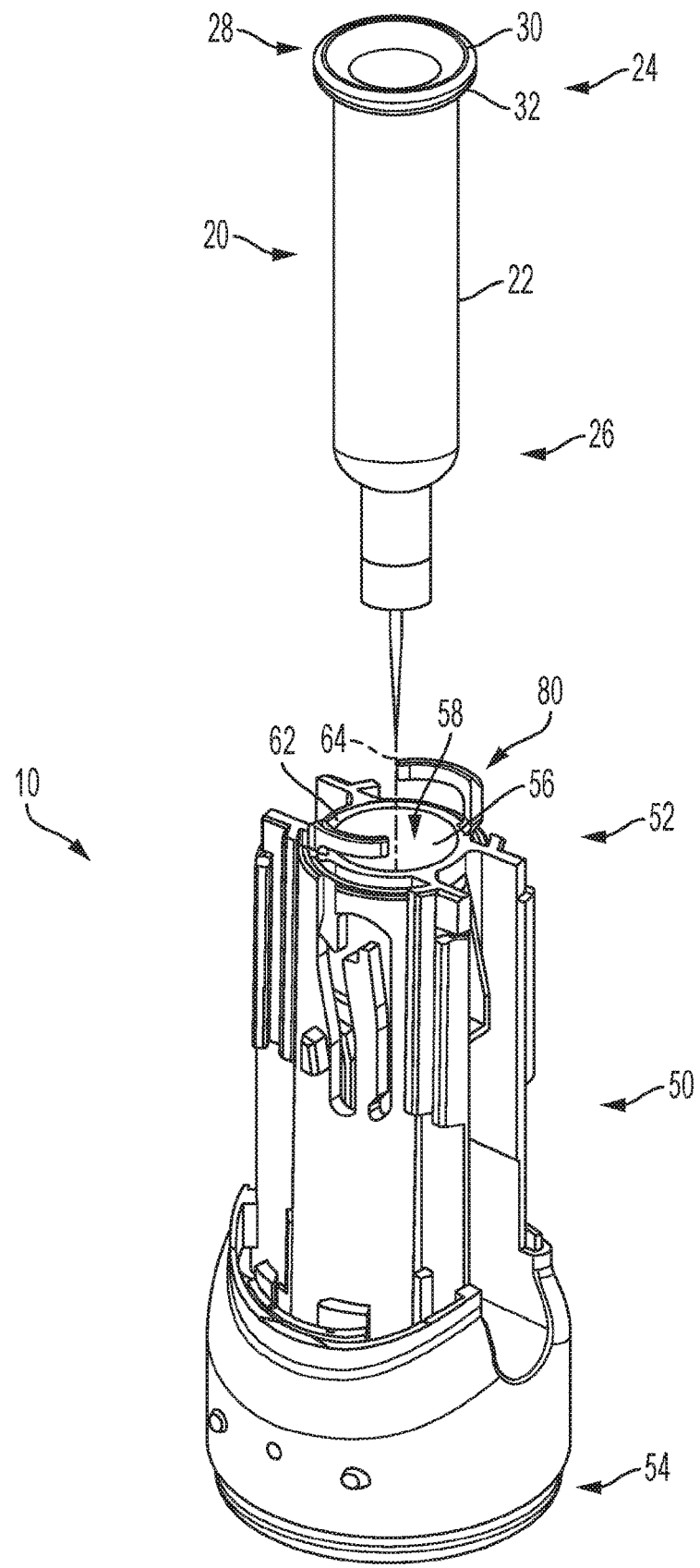
FIG. 1 is a front right view of a securing device according to a preferred embodiment of the invention and a syringe to be secured by the securing device, prior to the syringe being inserted into the securing device.
Figure 2:
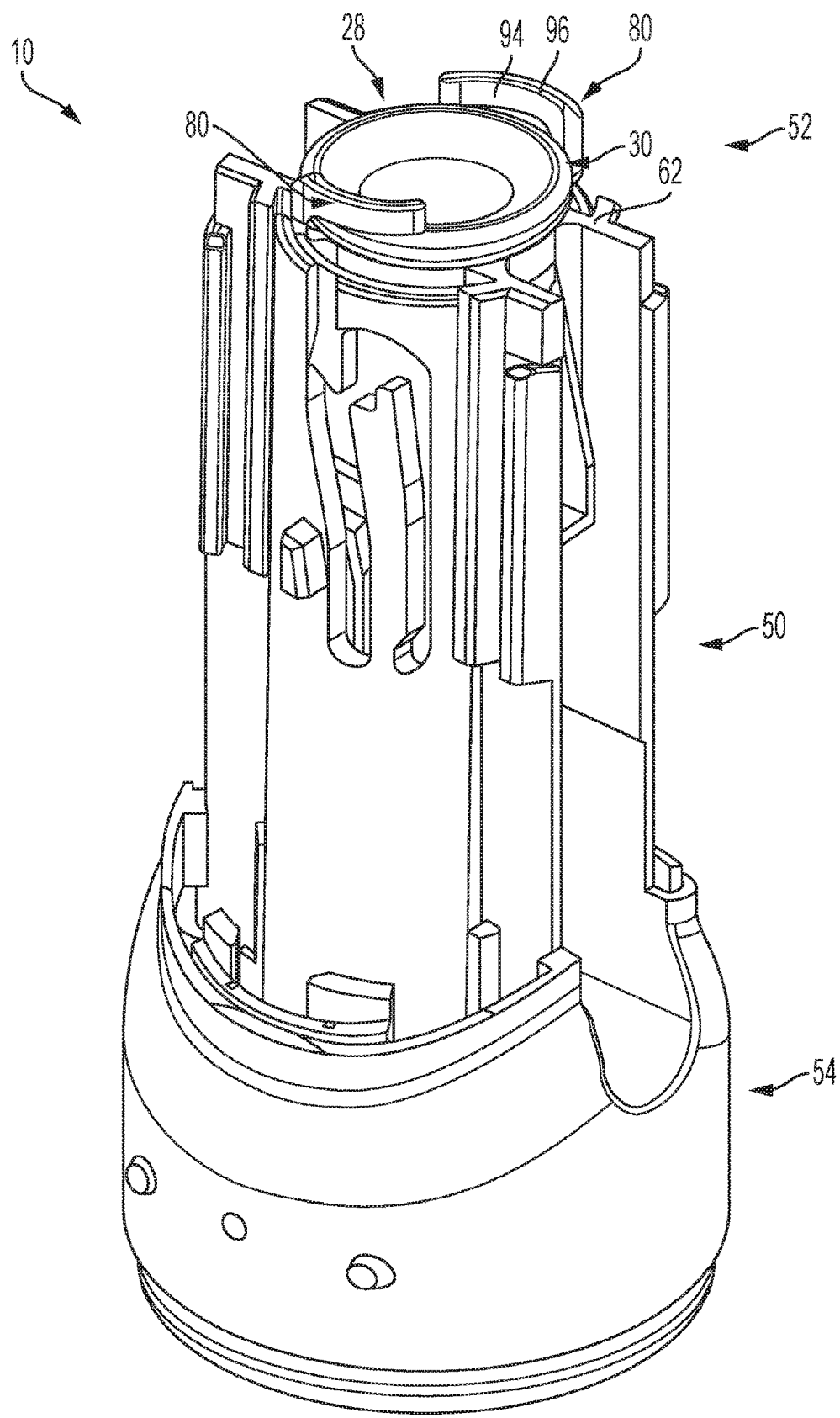
FIG. 2 is a front right perspective view of the securing device of FIG. 1, with the syringe of FIG. 1 secured therein.

Certain terminology is used in the following description for convenience only and is not limiting. The words "lower," "bottom," "upper," "top," "front," "back," and "rear" designate directions in the drawings to which reference is made. The words "inwardly" and "outwardly" refer to directions toward and away from, respectively, the geometric center of the component being discussed, and designated parts thereof, in accordance with the present disclosure. Unless specifically set forth herein, the terms "a," "an," and "the" are not limited to one element, but instead should be read as meaning "at least one." "At least one" may occasionally be used for clarity or readability, but such use is not change the interpretation of "a," "an," and "the." The terminology includes the words noted above, derivatives thereof, and words of similar import. References to a component extending, moving, or flexing in a particular direction refer to the component extending, moving, or flexing at least partially in the particular direction; an extension, movement, or flexion that includes any component of movement in the particular direction is included.

Referring to FIGS. 1 through 6, an example of a securing device 10 is disclosed for use with a syringe 20 having a barrel 22 with a proximal end portion 24 and a distal end portion 26, the proximal end portion 24 having a radially outwardly projecting flange 28, with the flange 28 having a proximally-facing surface 30 and a distally-facing surface 32. The flange 28 has a consistent rounded shape around the entire circumference of the barrel 22 of the syringe 20 depicted in FIGS. 1 through 6. The securing device 10 disclosed herein is also compatible with "cut" flanges, having one or more flat portions, as known in the art. The proximally-facing surface 30 may be flat or curved and may include a combination of curved and flat surfaces and may encompass any exterior surface of the flange 28 that is curved or faces at least partially proximally, including, for example, the surface portion 30a identified in FIGS. 3 and 4. The distally-facing surface 32 may be beveled, chamfered, curved, or otherwise contoured, and may be formed to promote the radially outward movement of the securing arm 80 or portions thereof, as described herein. The distally-facing surface 32 may encompass any exterior surface of the flange 28 that is curved or angled or faces at least partially distally.

The securing device is included in an injection device 10 and includes a body 50 having a proximal end portion 52 and a distal end portion 54. As shown in FIG. 1, the body 50 has an opening 56 in the proximal end portion 52 accessing an interior 58 of the body 50 for accepting the syringe 20. The body 50 preferably has a radially outwardly-facing outer surface 60 (FIGS. 3 and 4), which extends over the entire exterior side portion of the body 50. The body 50 also has a proximal end surface 62. The proximal end surface 62 of the body 50 is configured to contact the distally-facing surface 32 of the flange 30 of the syringe 20 when the syringe 20 is advanced distally into the opening 56, so that the flange 28 does not move distally past the proximal end surface 62 of the body 50. The body 50 may be a syringe housing or a portion thereof, and may include or cooperate with a needle shield for preventing accidental needle sticks.

Figure 3:
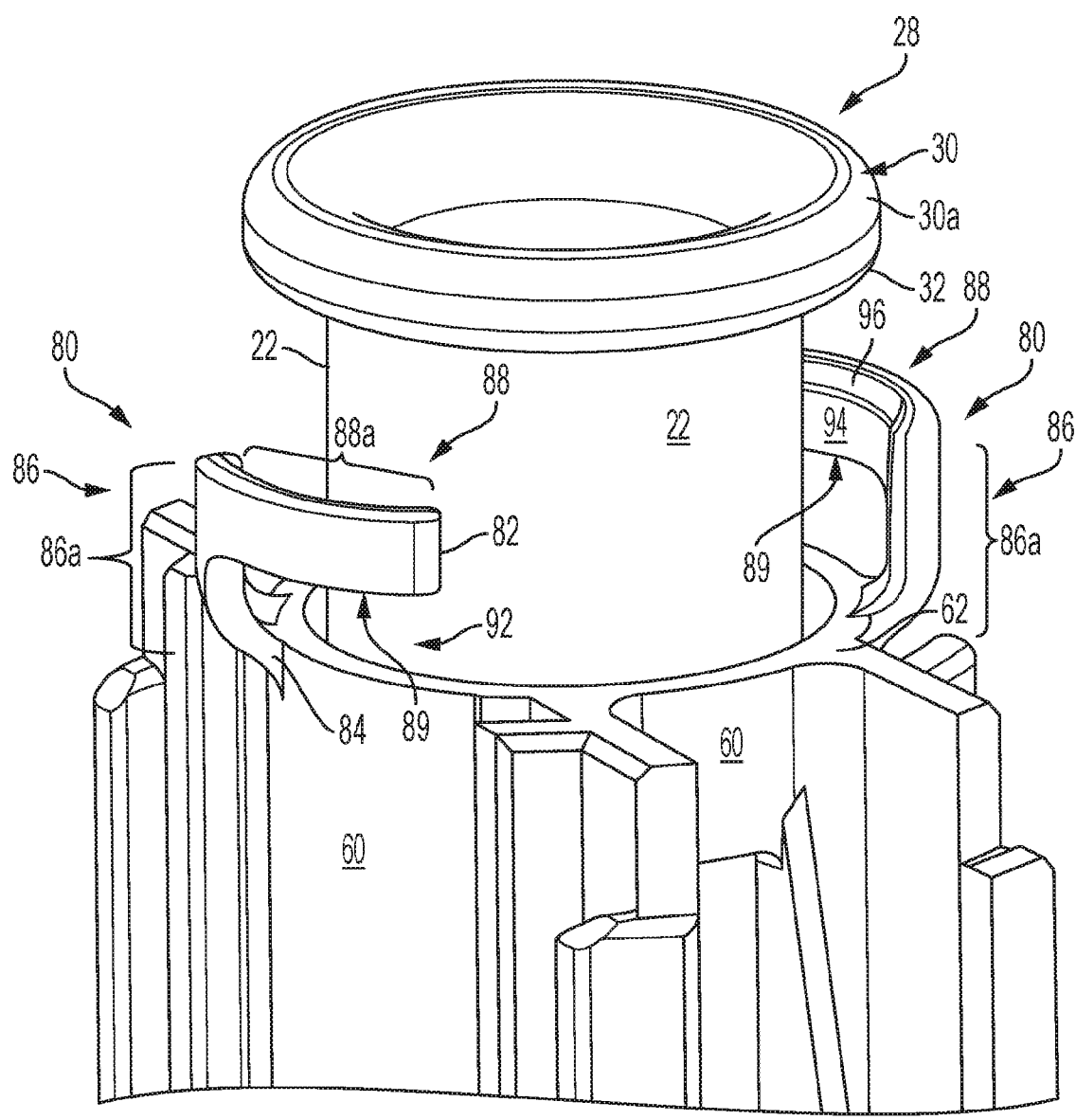
FIG. 3 is an enlarged front right partial perspective view of the securing device of FIG. 1 during insertion of the syringe, before the flange of the syringe has made contact with the securing device.
Figure 4:
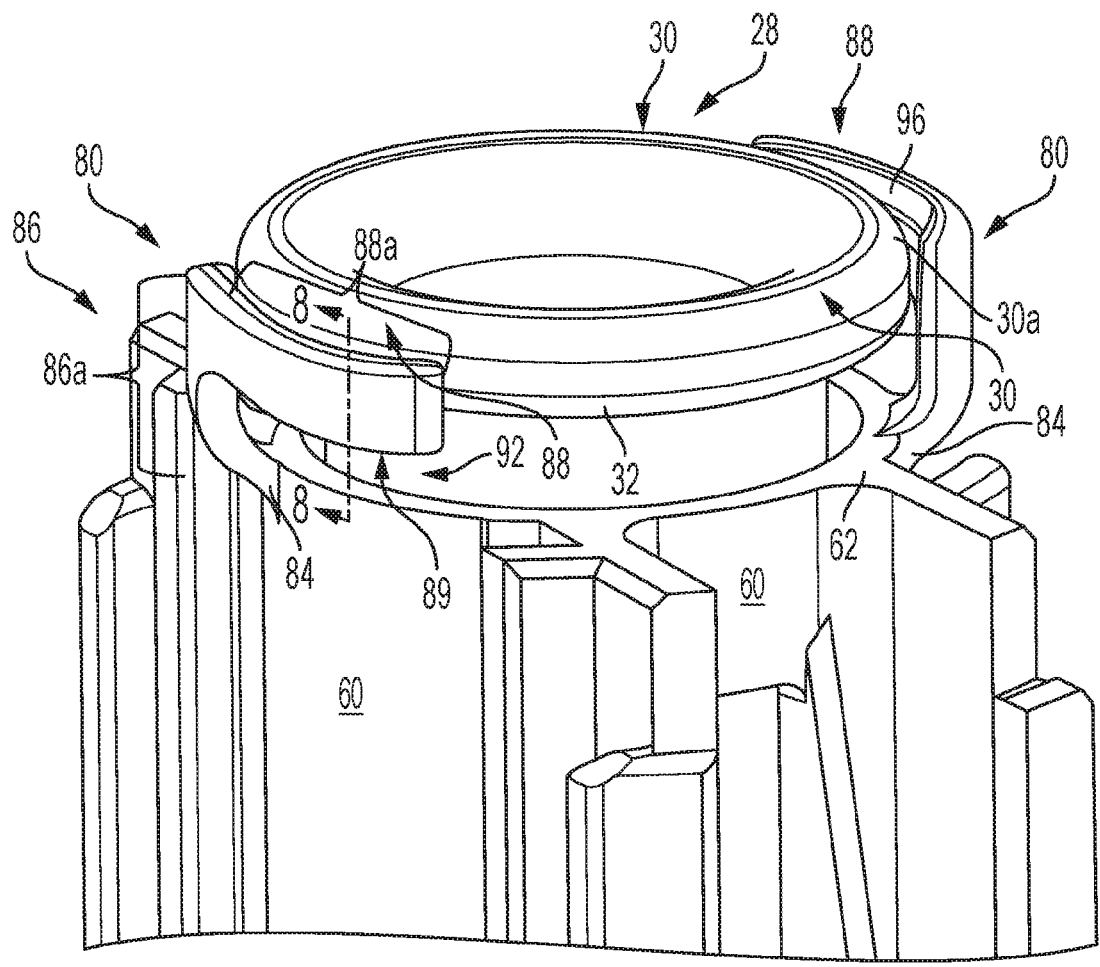
FIG. 4 is an enlarged front right partial perspective view of the securing device of FIG. 1 during insertion of the syringe, where the flange of the syringe is passing and in contact with two securing arms of the securing device.

Two securing arms 80 are depicted in the figures, but embodiments including additional securing arms 80, or only a single securing arm 80, are also within the scope of the disclosure. A single securing arm 80 is now described. As best seen in FIGS. 3 and 4, the securing arm 80 has a free end 82, a base end 84, a first portion 86, and a second portion 88. The base end 84 is preferably fixed to the outer surface 60 of the body.

Figure 5:
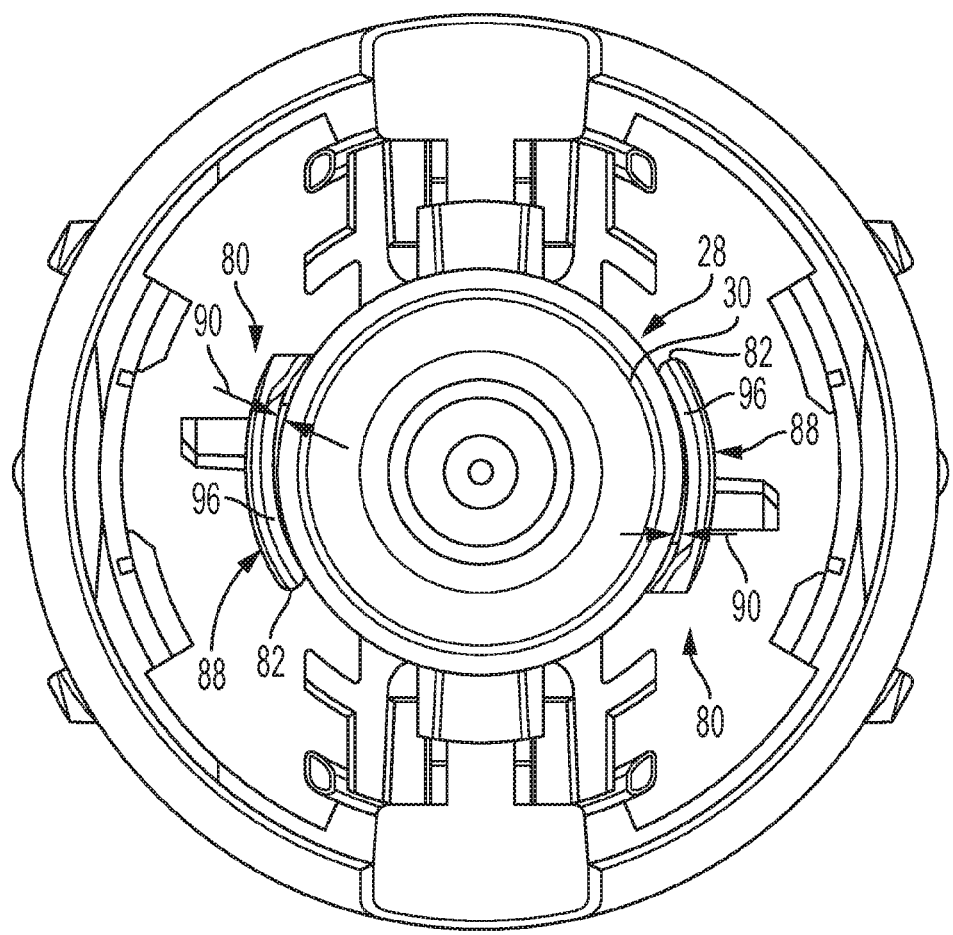
FIG. 5 is a top plan view of the securing device of FIG. 1, with the flange of the syringe passing and in contact with two securing arms of the securing device, as shown in FIG. 4.
Figure 6:
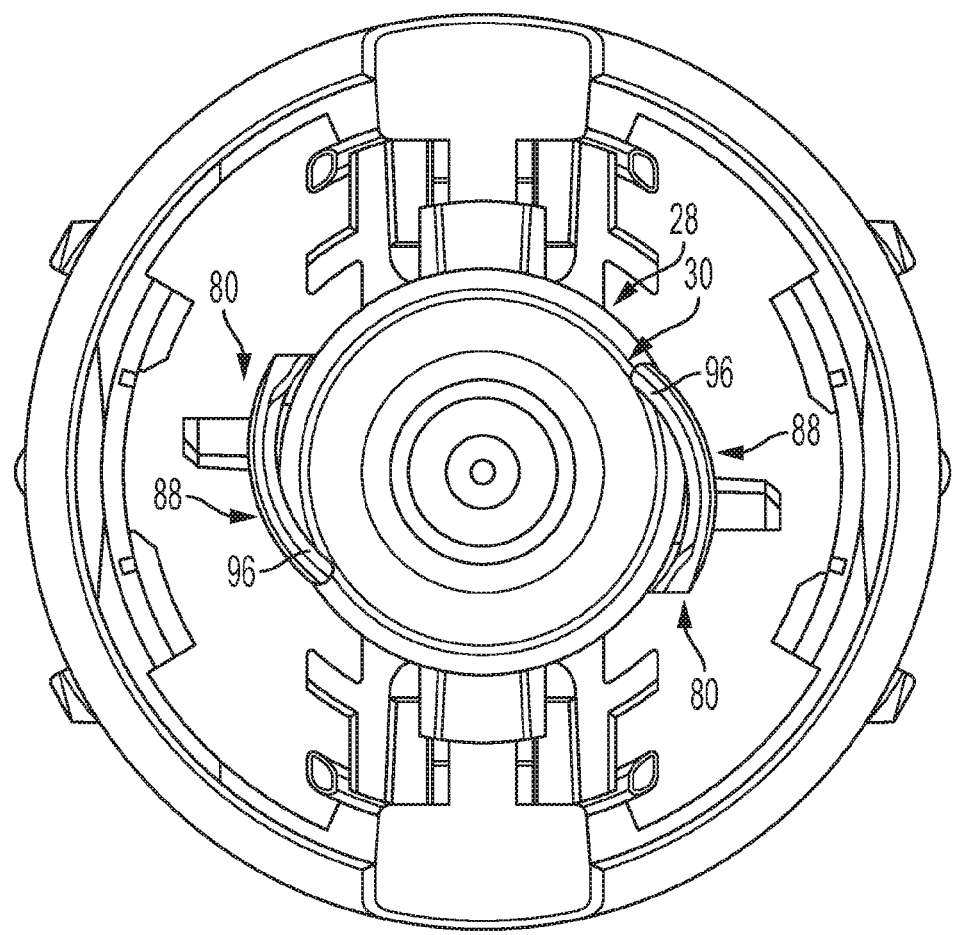
FIG. 6 is a top plan view of the securing device of FIG. 1, after the flange of the syringe has advanced distally past the securing arms, with the securing arms in a rest position preventing distal movement of the flange.

The first portion 86 of the securing arm 80 may extend radially outwardly from the base end 84 beyond the proximal end surface 62 of the body 50 to form a radial flange clearance 90 (FIG. 5). The radial flange clearance 90 permits the flange 28 to pass the first portion 86 as the syringe 20 is advanced distally into the opening 56. Note that the first portion 86 need not extend exclusively in a radially outward direction and as depicted extends both radially outwardly and proximally. The first portion 86 further extends proximally from the base end 84 beyond the proximal end surface 62 to form a flange gap 92 (best seen in FIGS. 3 and 4) between the proximal end surface 62 of the body 50 and a distally-facing surface 89 of the second portion 88 of the securing arm 80. As described above with respect to the distally-facing surface 32 of the flange 28, the distally-facing surface 89 of the securing arm 80 may similarly be curved and may encompass any exterior surface of securing arm 80 that is curved or faces at least partially distally. The second portion 88 is located proximally with respect to the flange gap 92 and extends at least partially radially inwardly toward the free end 82 in a rest position of the securing arm 80 (FIGS. 1, 2, 3, and 6). The second portion 88 contacts the flange 28 as the syringe 20 is advanced distally into the opening 56. The securing arm 80 is elastically flexible, and the free end 82 moves as a result of the combination of the securing arm 92 pivoting about the base 84 and elastically flexing. The arm 80 pivots and flexes so that the free end 82 moves between the rest position (shown in FIGS. 1, 2, 3, and 6) and a second position (FIGS. 4 and 5) when the flange 28 contacts the securing arm 80, causing the free end 82 of the securing arm 80 to move radially outwardly, through bending of the second portion 88 and/or other deformation of the securing arm 80, to allow the flange 28 to pass the second portion 88 as the syringe 20 is advanced distally into the opening 56. The free end 82 and the securing arm 80 also move distally in response to force exerted by the distally-facing surface 32 of the flange 28 as the flange 28 advances distally, but the securing arm 80 is preferably configured so that the securing arm is more flexible with respect to radial movement of the free end 82 than with respect to distal movement of the free end 82, with the result that the free end 82 moves farther radially outwardly than the free end 82 moves distally.

The securing arm 80, and as shown the second portion 88, preferably includes a proximal contact portion 96. The proximal contact portion 96 is configured, by being beveled, chamfered, or otherwise contoured, so that the distally-facing surface 32 of the flange 28 makes contact with the proximal contact portion 96 as the flange 28 advances distally. Moreover, the proximal contact portion 96 is configured so that the interaction between the distally-facing surface 32 and the proximal contact portion 96 causes the free end 82 of the securing arm 80 to move radially outwardly, through bending of the second portion 88 and/or other elastic deformation of the securing arm 80 (including deformation of the first portion 84), so that the free end 82 moves radially outwardly, allowing the flange 28 to pass the securing arm 80. The securing arm 80 is biased to the rest position such that after the flange 28 advances and passes the second portion 88, the distally-facing surface 89 of the second portion 88 is configured to contact the proximally-facing 30 surface of the flange 28 to prevent the flange 28 from moving proximally past the securing arm 80. As a result, the syringe 20 is secured to the body 50. When the securing arm 80 has returned to the rest position and is securing the syringe 20, the securing arm 80 preferably is under little or no elastic stress.

The first portion 86 of the securing arm 80 may extend substantially parallel with respect to a longitudinal axis 64 of the body (FIG. 1) and the second portion 88 of the securing arm 80 may extend substantially parallel to the proximal end surface 62 of the body 50. An inner surface 94 (FIGS. 2 and 3) of the second portion 88 of the securing arm 80 may be curved with a radius of curvature that preferably extends substantially radially into the body 50. For example, the second portion 88 may extend generally circumferentially around the opening 56 in the body, but with a slightly different curvature such that the free end 82, or at least part of the second portion 88, of the securing arm 80 resides, in the rest position, preferably in direct facing relation with a portion of the proximal end surface 62 of the body 50.

Figure 8:
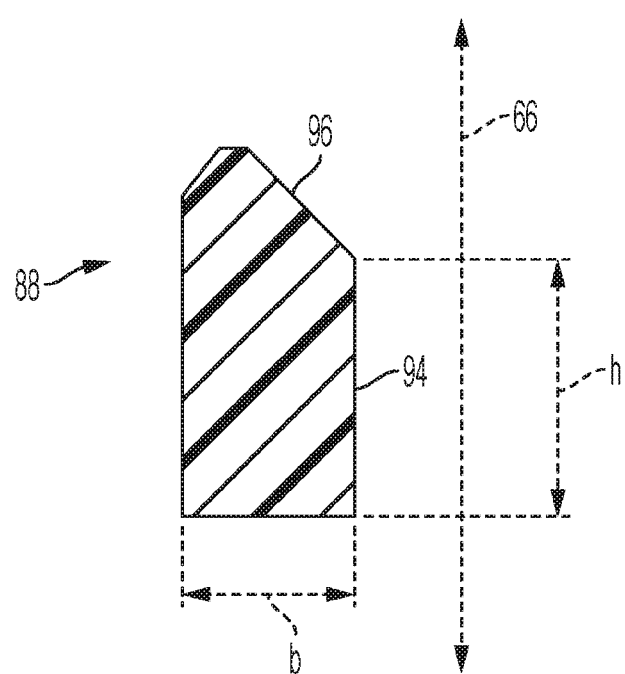
FIG. 8 is a cross-sectional view of the second portion 88 of the securing arm 80, taken along line A-A in FIG. 4.
Figure 9:
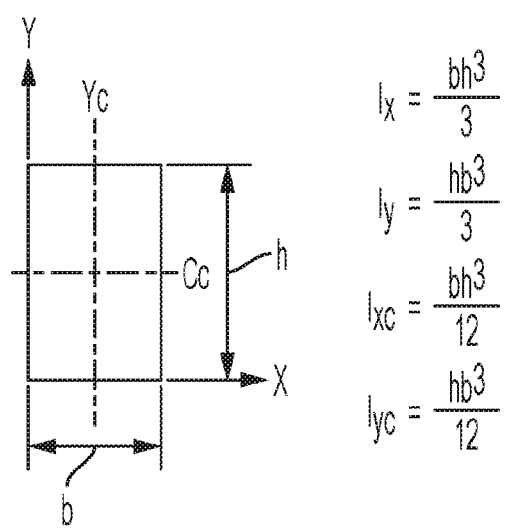
FIG. 9 is a view of a mathematical model for the resistance of a beam to a load in bending.

In certain embodiments, the securing arm 80 may take advantage of the fact that a beam, based on its geometric properties, may be more flexible with respect to bending on one plane, while being more resistant (stiffer) with respect to bending is a different plane. For example, the securing arm 80 may have a generally rectangular cross section (FIGS. 4, 8, and 9) and may have a greater cross-sectional dimension h in a direction parallel to the longitudinal axis 64 of the body 50 and a lesser dimension b in a direction perpendicular to the longitudinal axis 64. An approximate rigidity of the second portion 88 may be calculated, wherein the second portion 88 is treated as a rectangular beam having a bending torque applied through the center thereof, the bending torque being either in the proximal-distal direction or in the radial direction. The rigidity of the second portion 88 against proximal/distal bending may be calculated as $I_{XC}=b*h^3/12$, and the rigidity of the second portion 88 against radial bending may be calculated as $I_{YC}=h*b^3/12$. If h=2b, then we can calculate that $I_{XC}=8*I_{YC}$; in other words, the beam (as approximated) is about 8 times stiffer in proximal-distal bending than in radial bending. Similarly, the second portion 88 is substantially stiffer in the proximal-distal direction than in the radial direction. Moreover, the dimension of the securing arm 80, 180 at or near the base end 84, 184 may be selected in order to control the resistance of the securing arm 80, 180 to bending in the radial direction or in the proximal-distal direction. For example, referring to FIG. 10, the securing arm 180, in the base end 184 thereof, has a radial thickness 184a and a transverse width 184b. The radial thickness 184a and the transverse width 184b may preferably be selected so that the securing arm 180 is substantially stiffer with respect to movement of the free end 182 in the proximal-distal direction than in the radial direction. In the embodiment shown, the radial thickness 184a may be about 1 mm, with the transverse width being about 2 mm. A similar selection may be made to control the resistance of the securing arm 80 to movement of the free end 82 in the proximal-distal and radial directions.

In certain embodiments, the securing arm 80, 180, including but not limited to the second portion 88, 188, may have less resistance to radially outward movement of the free end 82, 182 than to distal or proximal movement of the free end 82, 182.

In certain embodiments, as shown, for example, in FIGS. 3 and 4, the first portion 86 of the securing arm 80 may have a first-portion length 86a parallel to the longitudinal axis 64 of the body 50, and the second portion 88 of the securing arm 80 may have a second-portion length 88a parallel to the proximal end surface 62 of the body 50, with the second-portion length 88a being about 2 to 3 times the first-portion length 86a. In one embodiment, the first-portion length 86a is about 4.3 mm, and the second-portion length 88a is about 8.3 mm, with ratio between the first-portion length 86a and the second-portion length 88a being about 1.9.

As noted above, and as shown in the drawings, the securing device may include a second securing arm 80, 180 located at an opposing side of the opening 56 of the body 50 from the first securing arm 80, 180.

Preferably the dimensions of the securing arm 80, 180, or of each securing arm 80, 180 where multiple securing arms are present, are selected so that at least the second portion 88, 188 of the securing arm 80, 180 is more flexible when the free end 82, 182 is pivoting radially outwardly than when pivoting proximally away from the proximal end surface 62 of the body 50. As a result, only a relatively low force is required to advance the syringe 20 distally into the opening 56 of the body 50, whereas the securing arm 80, 180, once returned to the rest position, resists proximal movement of the syringe 20, thus securing the syringe 20 to the body 50 and limiting the potential for removal therefrom. The securing arm 80, 180 as described herein has the advantage of not relying upon friction between the body 50 or opening 56 and the syringe 20 or a separate adapter into which a syringe 20 must be placed. The result is that the securing arm 80, 180 functions reliably without requiring highly precise dimensions, surface characteristics, or freedom from contamination, as may be required in a friction-based securing device.

Figure 7:
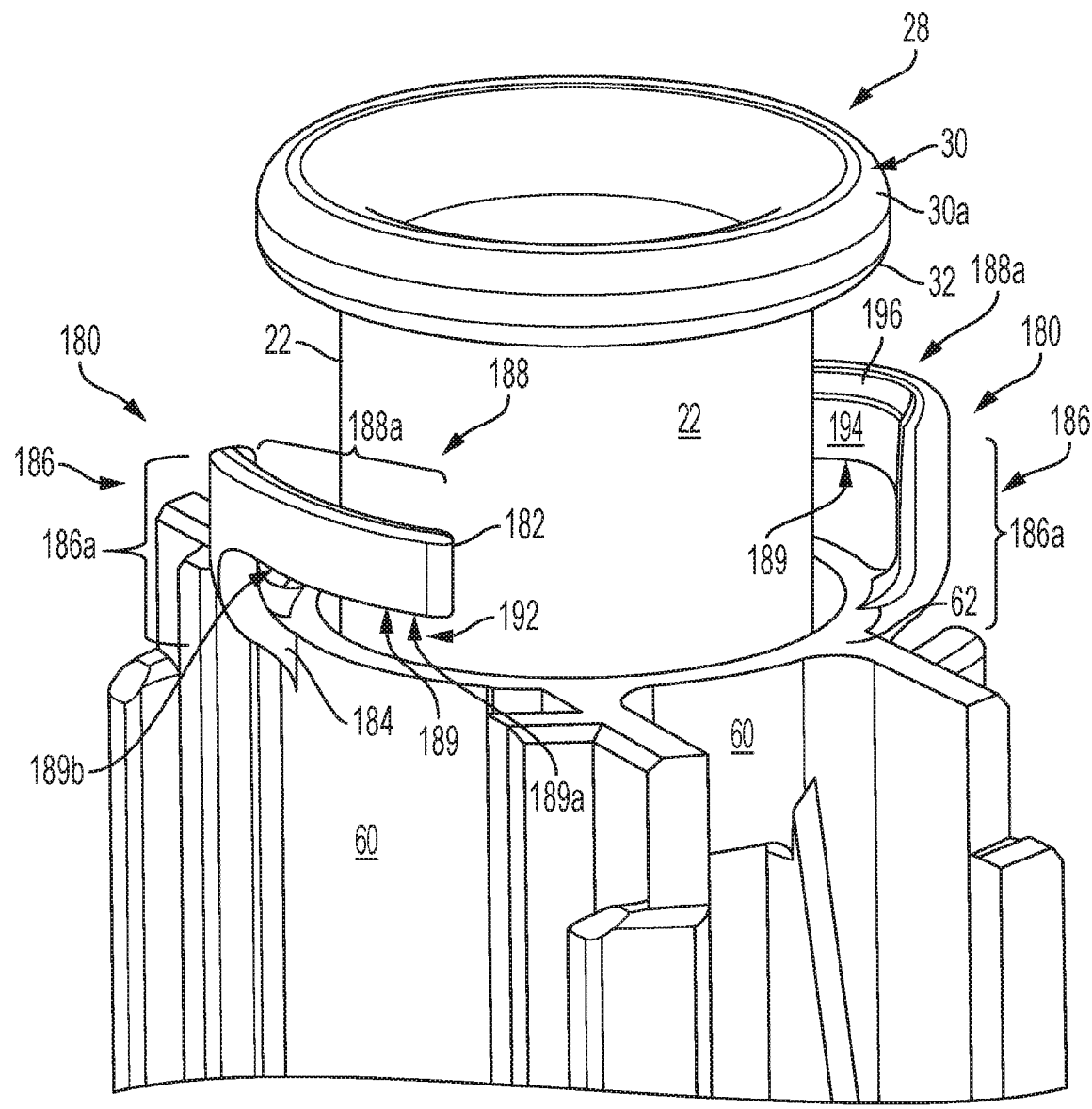
FIG. 7 is an enlarged front right partial perspective view of a second embodiment of securing device having securing arms that slope distally, shown during insertion of the syringe, before the flange of the syringe has made contact with the securing device.
Figure 10:
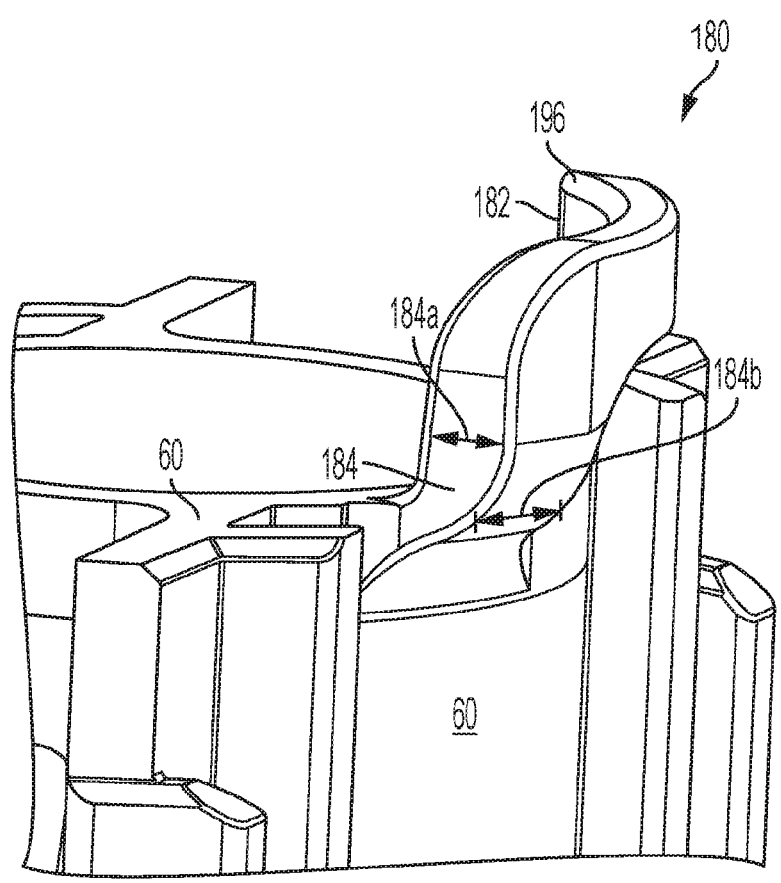
FIG. 10 is an enlarged partial perspective view of a the securing device of FIG. 1.

Referring to FIGS. 7 and 10, an alternative embodiment of a securing arm 180, is substantially the same in structure and function as the securing arm 80 of FIGS. 1-6, except as noted herein. The first portion 186 of the securing arm 180 may extend radially outwardly from the base end 184 beyond the proximal end surface 62 of the body 50 to form a radial flange clearance (not shown in FIGS. 7 and 10 but substantially the same as the radial flange clearance 90 shown in FIG. 5) permitting the flange 28 to pass the first portion 186 as the syringe 20 is advanced distally into the opening 56.

The first portion 186 need not extend exclusively in a radially outward direction and as depicted extends both radially outwardly and proximally. The first portion 186 further extends proximally from the base end 184 beyond the proximal end surface 62 to form a flange gap 192 between the proximal end surface 62 of the body 50 and a distally-facing surface 189 of the second portion 188 of the securing arm 180. In certain embodiments, the first portion 186 of the securing arm 180 may have a first-portion length 186a parallel to the longitudinal axis 64 of the body 50, and the second portion 188 of the securing arm 180 may have a second-portion length 188a parallel to the proximal end surface 62 of the body 50, with the respective lengths 186a and 188a being related as described above with respect to the securing arm 80. The second portion 188 may have an inner surface 194, and the inner surface 194 may be curved with a radius of curvature that preferably extends substantially radially into the body 50. As described above with respect to the distally-facing surface 32 of the flange 28, the distally-facing surface 189 of the securing arm 180 may similarly be contoured and may encompass any exterior surface of securing arm 180 that is curved or faces at least partially distally.

The distally-facing surface 189 may slope distally over at least a portion of the length of the second portion 188 from the base end 184 to the free end 182. The second portion 88 is located proximally with respect to the flange gap 192 and extends at least partially radially inwardly toward the free end 182 in a rest position of the securing arm 180, as discussed with respect to the securing arm 80 (FIGS. 1, 2, 3, and 6). The second portion 188 contacts the flange 28 as the syringe 20 is advanced distally into the opening 56. The securing arm 180 is elastically flexible and pivots radially between the rest position (shown in FIGS. 1, 2, 3, and 6) and a second position (FIGS. 4 and 5) when the flange 28 contacts the securing arm 180, causing the free end 182 of the securing arm 180 to move radially outwardly, through bending of the second portion 188 and/or other deformation of the securing arm 180, to allow the flange 28 to pass the second portion 188 as the syringe 20 is advanced distally into the opening 56. The securing arm 180, and as shown the second portion 188, preferably includes a proximal contact portion 196. The proximal contact portion 196 is configured, by being beveled, chamfered, or otherwise contoured, so that the distally-facing surface 32 of the flange 28 makes contact with the proximal contact portion 196 as the flange 28 advances distally. Moreover, the proximal contact portion 196 is configured so that the interaction between the distally-facing surface 32 and the proximal contact portion 196 causes the free end 182 of the securing arm 180 to move radially outwardly, through bending of the second portion 188 and/or other elastic deformation of the securing arm 180, so that the free end 182 moves radially outwardly, allowing the flange 28 to pass the securing arm 180. The securing arm 180 is biased to the rest position such that after the flange 28 advances and passes the second portion 188, the distally-facing surface 189 of the second portion 188 is configured to contact the proximally-facing 30 surface of the flange 28 to prevent the flange 28 from moving proximally past the securing arm 180. In the securing arm 180, the distally-facing surface 189 of the second portion 188 of the securing arm is configured so that a first portion 189a of the distally-facing surface nearer the free end of the securing arm is positioned distally with respect to a second portion 189b of the distally-facing surface nearer the base 184; this configuration may aid in securing syringes 20 having flanges 28 of differing thicknesses. As a result, the syringe 20 is secured to the body 50.

The securing devices described herein may be advantageously used with, for example, a device of the type disclosed in U.S. Pat. No. 9,216,256 to Olsen et al. and U.S. Pat. No. 9,233,213 to Olsen et al. both of which are incorporated by reference herein.

Figure 11:
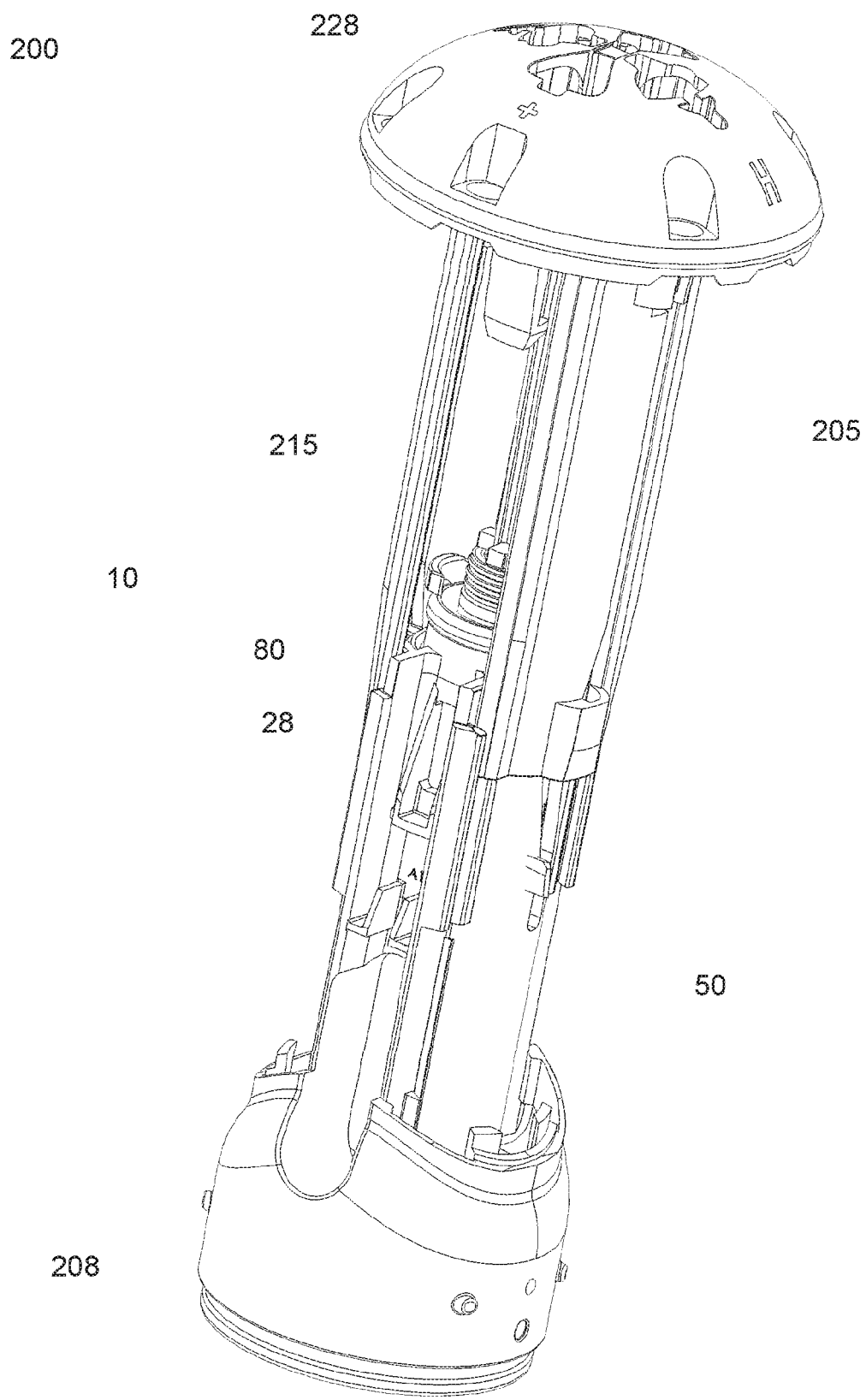
FIG. 11 is a perspective view of the securing device of FIG. 1 incorporated in a hand-held injection device.

Referring to FIG. 11, an exemplary hand-held injection device 200 includes an upper housing 205 configured to receive a manual force via a grip cap 228 and move with respect to a lower housing, the body 50, distally from a pre-use position to a dispensed position in response to the manual force. A needle guard 208 is movable relative to the body 50 proximally from a first position. The needle guard 208 extends from the body 50 distally, so as to be configured to cover, when the syringe (only the flange 30 is visible in FIG. 11) is secured in the body 50, the needle as the needle extends from the lower housing distally, to a second position, wherein the needle guard 208 is retracted relative to the tip of the needle so as to expose the tip of the needle. The upper housing 205 is supported relative to the lower housing, the body 50. A plunger rod 215 is carried by the upper housing 205 and movable with the upper housing 205 so as to advance relative to the syringe when the upper housing 205 is moved distally. Advancement of the plunger rod 215 relative to the syringe causes the syringe to deliver the medication through the needle thereof.

The devices and components described herein may be made of polymers or other materials of sufficient strength, heat resistance, corrosion resistance, and other properties to support operation of the devices and components as described herein. Suitable materials are known in the art.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

I claim:

1. A securing device for an injection device configured to receive a syringe, the syringe comprising a barrel having a proximal end portion and a distal end portion, the proximal end portion comprising a flange that projects radially outward, the flange defining a proximally-facing surface and a distally-facing surface, the securing device comprising:
    a body comprising:
        a proximal end portion;
        a distal end portion;
        an opening in the proximal end portion extending to an interior of the body, the opening configured to accept the syringe;
        a radially-outwardly facing outer surface; and
        a proximal end surface being configured to contact the distally-facing surface of the flange of the syringe when the syringe is advanced distally into the opening, so that the flange does not move distally past the proximal end surface of the body; and
    a securing arm comprising:
        a free end;
        a base end fixed directly to the radially-outwardly facing outer surface of the body;
        a first portion extending away from the base end beyond the proximal end surface of the body in a radial direction to define a radial flange clearance between the securing arm and the body along the radial direction permitting the flange to pass the first portion as the syringe is advanced distally into the opening; and
        a second portion,
    wherein the first portion extends proximally from the base end beyond the proximal end surface to define a flange gap between the proximal end surface of the body and a distally-facing surface of the second portion,
    wherein the second portion is located proximally with respect to the flange gap and defines an inner surface with a concavity that extends generally circumferentially around the opening in the body and at least partially radially inwardly toward the free end in a rest position of the securing arm,
    wherein the second portion is configured to contact the flange as the syringe is advanced distally into the opening,
    wherein the securing arm is elastically flexible to permit at least the free end to move radially outwardly relative to the body to allow the flange to pass the first portion as the syringe is advanced distally into the opening, and
    wherein the securing arm is biased to the rest position such that, after the flange passes the second portion, the distally-facing surface of the second portion is configured to contact the proximally-facing surface of the flange to prevent the flange from moving proximally past the securing arm.

2. The securing device of claim 1, wherein the first portion of the securing arm extends substantially parallel with respect to a longitudinal axis of the body and the second portion of the securing arm extends substantially parallel to the proximal end surface of the body.

3. The securing device of claim 2, wherein an inner surface of the second portion of the securing arm is curved with a radius of curvature that extends substantially radially into the body.

4. The securing device of claim 2, wherein the securing arm has a first flexibility with respect to radially outward movement of the free end of the securing arm with respect to the body, and a second flexibility with respect to proximal movement of the free end of the securing arm with respect to the body, and the first flexibility is greater than the second flexibility.

5. The securing device of claim 2, wherein the first portion of the securing arm has a first-portion length parallel to the longitudinal axis of the body, and the second portion of the securing arm has a second-portion length parallel to the proximal end surface of the body, and the second-portion length is greater than the first-portion length.

6. The securing device of claim 1, wherein the securing arm has a first flexibility with respect to radially outward movement of the free end of the securing arm with respect to the body, and a second flexibility with respect to proximal movement of the free end of the securing arm with respect to the body, and the first flexibility is greater than the second flexibility.

7. The securing device of claim 1, further comprising a second securing arm comprising:
    a free end;
    a base end fixed directly to the radially-outwardly facing outer surface of the body;
    a first portion that extends radially outwardly from the base end of the second securing arm beyond the proximal end surface of the body to define a radial flange clearance permitting the flange to pass the second portion as the syringe is advanced distally into the opening; and
    a second portion,
    wherein the first portion of the second securing arm extends proximally from the base end of the second securing arm beyond the proximal end surface to define a flange gap between the proximal end surface of the body and a distally-facing surface of the second portion of the second securing arm,
    wherein the second portion of the second securing arm is located above the flange gap of the second securing arm and defines an inner surface with a concavity that extends at least partially radially inwardly toward the free end of the second securing arm in a rest position of the securing arm, wherein the second portion of the second securing arm contacts the flange as the syringe is advanced distally into the opening, wherein the second securing arm is elastically flexible to permit at least the free end of the second securing arm to move radially outwardly relative to the body to allow the flange to pass the second portion of the second securing arm as the syringe is advanced distally into the opening, and wherein the second securing arm is biased to the rest position such that, after the flange passes the second portion of the second securing arm, the distally-facing surface of the second portion of the second securing arm is configured to contact the proximally-facing surface of the flange to prevent the flange from moving proximally past the second securing arm.

8. The securing device of claim 7, wherein the first portion of the second securing arm extends substantially parallel with respect to a longitudinal axis of the body and the second portion of the second securing arm extends substantially parallel to the proximal end surface of the body.

9. The securing device of claim 8, wherein an inner surface of the second portion of the second securing arm is curved with a radius of curvature that extends substantially radially into the body.

10. The securing device of claim 8, wherein the second securing arm has a first flexibility with respect to radially outward movement of the free end of the second securing arm with respect to the body, and a second flexibility with respect to proximal movement of the free end of the second securing arm with respect to the body, and the first flexibility is greater than the second flexibility.

11. The securing device of claim 8, wherein the first portion of the second securing arm has a first-portion length parallel to the longitudinal axis of the body, and the second portion of the second securing arm has a second-portion length parallel to the proximal end surface of the body, and the second-portion length is greater than the first-portion length.

12. The securing device of claim 7, wherein the second securing arm has a first flexibility with respect to radially outward movement of the free end of the second securing arm with respect to the body, and a second flexibility with respect to proximal movement of the free end of the second securing arm with respect to the body, and the first flexibility is greater than the second flexibility.

13. The securing device of claim 1, wherein the securing arm defines a contoured surface for contacting the flange as the syringe advances distally, the contoured surface being configured such that at least the free end of the securing arm moves radially outwardly to allow the flange of the syringe to pass.

14. The securing device according to claim 13, wherein the contoured surface defines a beveled surface.

15. The securing device of claim 1, wherein the distally-facing surface of the second portion of the securing arm is configured such that a first portion of the distally-facing surface is nearer the free end of the securing arm and is positioned distally with respect to a second portion of the distally-facing surface nearer the base end.

16. The securing device of claim 1, wherein the securing arm is configured to hinge about an axis extending longitudinally through the first portion.

17. The securing device of claim 1, wherein the inner surface with the concavity of the second portion extends generally circumferentially between the base end and the free end.

18. The securing device of claim 1, wherein the radial flange clearance is defined between an inwardly-facing surface of the securing arm and the radially-outwardly facing outer surface of the body along the radial direction.

19. The securing device of claim 1, wherein the second portion extends from the first portion at the radial flange clearance generally circumferentially around the opening in the body to the free end at which the securing arm terminates, and the free end extends proximally.

20. A hand-held injection device which can receive a syringe prefilled with a drug and having a needle, the syringe comprising a barrel having a proximal end portion and a distal end portion, the proximal end portion comprising a flange that projects radially outward, the flange defining a proximally-facing surface and a distally-facing surface, the hand-held injection device comprising:

a body comprising:
a proximal end portion;
a distal end portion;
an opening in the proximal end portion extending to an interior of the body, the opening configured to accept the syringe;
a radially-outwardly facing outer surface; and
a proximal end surface being configured to contact the distally-facing surface of the flange of the syringe when the syringe is advanced distally into the opening, so that the flange does not move distally past the proximal end surface of the body;

a securing arm comprising:
a free end;
a base end fixed directly to the radially-outwardly facing outer surface of the body;
a first portion extending away from the base end beyond the proximal end surface of the body in a radial direction to define a radial flange clearance between the securing arm and the body along the radial direction permitting the flange to pass the first portion as the syringe is advanced distally into the opening; and
a second portion;

a needle guard, that is movable relative to the body proximally from a first position, wherein the needle guard extends from the body distally, so as to be configured to cover, when the syringe is secured in the body, the needle extending from a lower housing distally, to a second position, wherein the needle guard is retracted relative to a tip of the needle so as to expose the tip of the needle;

an upper housing supported relative to the lower housing, the upper housing configured to receive a manual force and move with respect to the lower housing distally from a pre-use position to a dispensed position in response to the manual force; and a plunger rod carried by the upper housing and movable with the upper housing so as to advance relative to the syringe when the upper housing is moved distally, wherein the first portion extends proximally from the base end beyond the proximal end surface to define a flange gap between the proximal end surface of the body and a distally-facing surface of the second portion, wherein the second portion is located proximally with respect to the flange gap and defines an inner surface with a concavity that extends generally circumferentially around the opening in the body and at least partially radially inwardly toward the free end in a rest position of the securing arm,
wherein the second portion is configured to contact the flange as the syringe is advanced distally into the opening,
wherein the securing arm is elastically flexible to permit at least the free end to move radially outwardly relative to the body to allow the flange to pass the first portion as the syringe is advanced distally into the opening, and
wherein the securing arm is biased to the rest position such that after the flange passes the second portion, the distally-facing surface of the second portion is configured to contact the proximally-facing surface of the flange to prevent the flange from moving proximally past the securing arm.

21. The hand-held injection device of claim 20, wherein the securing arm is configured to hinge about an axis extending longitudinally through the first portion.

22. The hand-held injection device of claim 20, wherein the inner surface with the concavity of the second portion extends generally circumferentially between the base end and the free end.

23. The hand-held injection device of claim 20, wherein the radial flange clearance is defined between an inwardly-facing surface of the securing arm and the radially-outwardly facing outer surface of the body along the radial direction.

24. The hand-held injection device of claim 20, wherein the second portion extends from the first portion at the radial flange clearance generally circumferentially around the opening in the body to the free end at which the securing arm terminates, and the free end extends proximally.

25. A hand-held injection device comprising:
a securing device for the injection device according to claim 1;
a needle guard that is movable relative to the body proximally from a first position, wherein the needle guard extends from the body distally, so as to be configured to cover, when the syringe is secured in the body, a needle extending from a lower housing distally, to a second position, wherein the needle guard is retracted relative to a tip of the needle so as to expose the tip of the needle;
an upper housing supported relative to the lower housing, the upper housing configured to receive a manual force and move with respect to the lower housing distally from a pre-use position to a dispensed position in response to the manual force; and
a plunger rod carried by the upper housing and movable with the upper housing so as to advance relative to the syringe when the upper housing is moved distally, wherein advancement of the plunger rod relative to the syringe causes the syringe to deliver a medication out the needle.

26. The hand-held injection device of claim 25, further comprising the syringe, wherein the syringe is prefilled and is configured to be inserted into the body and to be secured by the securing device.

* * * * *